United States Patent [19]

Kawauchi et al.

[11] Patent Number: 4,772,700

[45] Date of Patent: Sep. 20, 1988

[54] SPIROPIPERIDINENAPHTHOXAZINE COMPOUND

[75] Inventors: Susumu Kawauchi, Kawasaki; Shigeru Saeda, Tokyo; Haruo Yoshida, Oita, all of Japan

[73] Assignee: Showa Denko Kabushiki Kaisha, Tokyo, Japan

[21] Appl. No.: 94,488

[22] PCT Filed: Dec. 19, 1986

[86] PCT No.: PCT/JP86/00642

§ 371 Date: Aug. 19, 1987

§ 102(e) Date: Aug. 19, 1987

[87] PCT Pub. No.: WO87/03874

PCT Pub. Date: Jul. 2, 1987

[30] Foreign Application Priority Data

Dec. 19, 1985 [JP] Japan .................. 60-284401

[51] Int. Cl.⁴ .......................... C07D 498/10
[52] U.S. Cl. ........................................ 544/71
[58] Field of Search ........................... 544/71

[56] References Cited

U.S. PATENT DOCUMENTS

| | | | |
|---|---|---|---|
| 3,562,172 | 2/1971 | Ono et al. | 252/300 |
| 4,342,668 | 8/1982 | Hovey et al. | 252/586 |
| 4,636,561 | 1/1987 | Hosoda | 544/71 |
| 4,699,473 | 10/1987 | Chu | 350/409 |

FOREIGN PATENT DOCUMENTS 23787 3/1973 Japan .
44180 6/1973 Japan .

Primary Examiner—Richard L. Raymond
Attorney, Agent, or Firm—Sughrue, Mion, Zinn, Macpeak & Seas

[57] ABSTRACT

A spiropiperidine-naphthoxazine compound represented by the following general formula (I) is valuable as a photochromic compound:

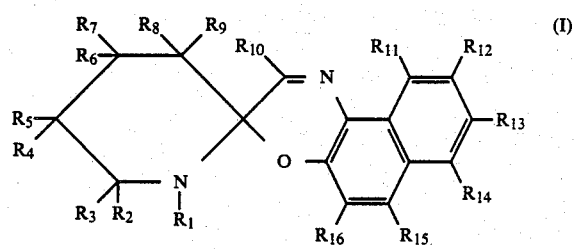

wherein (a) $R_1$ represents a C1–C18 alkyl group, C7–C15 aralkyl group which may be substituted, a C1–C10 alkenyl group or a C6–C15 aryl group which may be substituted, (b) $R_2$ through $R_9$ represent a group $R_1$ defined above, a hydrogen atom, or a C5–C10 alicyclic ring or a norbonyl or adamantyl group, which is bonded between groups present on one skeleton carbon atom or between groups on adjacent skeleton carbon atoms (at the ortho-position), (c) $R_{10}$ represents a C1–C18 alkyl group, a C7–C15 aralkyl group which may be substituted or a C1–C10 alkenyl group, and (d) $R_{11}$ through $R_{16}$ represent a hydrogen atom, a C1–C9 alkyl group, a C1–C5 alkoxyl group, a halogen atom, a nitro group or a cyano group.

2 Claims, 4 Drawing Sheets

SPIROPIPERIDINENAPHTHOXAZINE COMPOUND

DESCRIPTION

1. Technical Field

The present invention relates to a novel spiropiperidine-naphthoxazine compound. More particularly, it relates to a spiropiperidine-naphthoxazine compound having photochromic characteristics giving an excellent repeatability.

2. Background Art

By photochromism is meant a reversible phenomenon wherein the color of a compound is changed under irradiation with light containing ultraviolet rays, such as sunlight or the light of a mercury lamp, and when the compound is placed in the dark place and irradiation is stopped, the original color is restored. A compound exhibiting this phenomenon is called "a photochromic compound".

Many photochromic compounds have been heretofore synthesized but very few compounds are practically used on an industrial scale. This is because, when photochromic compounds are used several times repeatedly, the photochromic compounds are deteriorated and they fail to show a photochromism or the color quality is degraded. Because of this defect, although many photochromic compounds and their applications have been proposed in patent publications and the other literatures, only a limited number of compounds are practically used.

Recently, a photochromic compound having a relatively good adaptability to repeated use has been proposed, for example, by H. G. Heller et al in J. Chem. Soc. Perkin Trans. I, 1981, page 202. However, this photochromic compound still has an insufficient adaptability to repeated use.

DISCLOSURE OF THE INVENTION

We carried out research with a view to overcoming the above-mentioned problems of the conventional technique and improving the adaptability to repeated use of a photochromic compound. As the result, we found chromic compounds having an excellent adaptability to repeated used and have now completed the present invention based on this finding.

More specifically, in accordance with the present invention, there is provided a spiropiperidine-naphthoxazine compound represented by the following general formula (I):

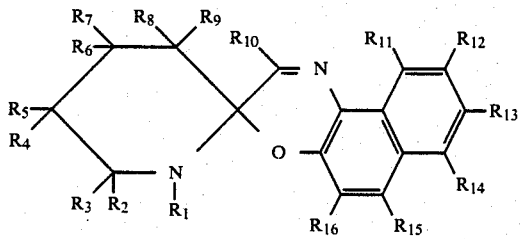

wherein (a) $R_1$ represents a linear or branched alkyl group having 1 to 18 carbon atoms, an aralkyl group having 7 to 15 carbon atoms, which may be substituted, an alkenyl group having 1 to 10 carbon atoms or an aryl group having 6 to 15 carbon atoms, which may be substituted, (b) $R_2$, $R_3$, $R_4$, $R_5$, $R_6$, $R_7$, $R_8$, and $R_9$ represent independently a group $R_1$ defined above, a hydrogen atom or an alicyclic ring having 5 to 10 carbon atoms or a norbonyl or adamantyl group, which is bonded between groups present on one skeleton carbon atom or between groups present on adjacent skeleton carbon atoms (at the ortho-position), (c) $R_{10}$ represents a hydrogen atom, a linear or branched alkyl group having 1 to 18 carbon atoms, an aralkyl group having 7 to 15 carbon atoms, which may be substituted, or an alkenyl group having 1 to 10 carbon atoms, and (d) $R_{11}$, $R_{12}$, $R_{13}$, $R_{14}$, $R_{15}$, and $R_{16}$ represent independently a hydrogen atom, a linear or branched alkyl group having 1 to 9 carbon atoms, an alkoxyl group having 1 to 5 carbon atoms, a halogen atom, a nitro group or a cyano group.

BEST MODE FOR CARRYING OUT THE INVENTION

Figure 1:
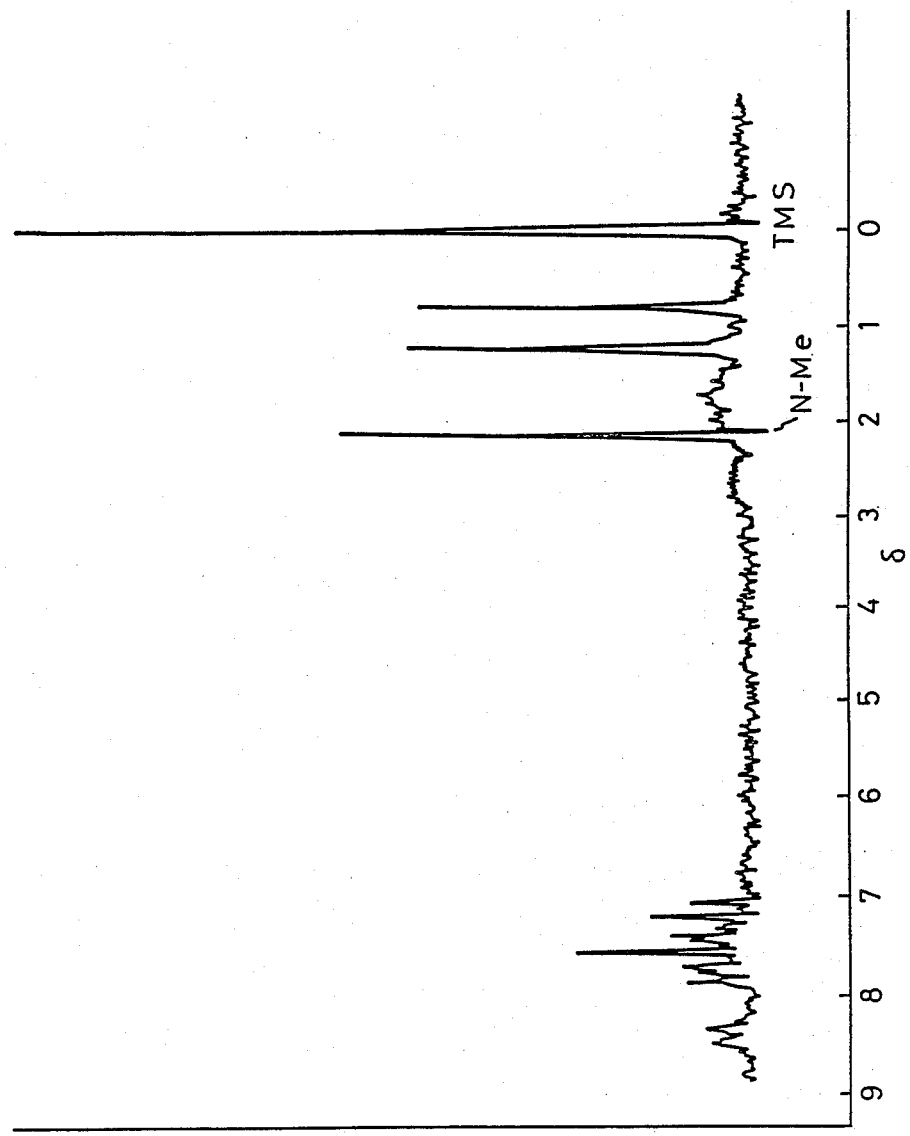
FIG. 1 shows an NMR spectrum of the compound prepared in Example 1.

The spiropiperidine-naphthoxazine compound of the present invention is a novel compound not disclosed in any literature reference. Preferred examples are compounds of the above-mentioned general formula (I) in which (a) $R_1$ represents a linear or branched alkyl group having 1 to 4 carbon atoms, (b) $R_2$, $R_3$, $R_4$, $R_5$, $R_6$, and $R_7$ represent independently a hydrogen atom, a methyl group or an ethyl group, (c) $R_8$ and $R_9$ represent independently a methyl group or an ethyl group, (d) $R_{10}$ represents a hydrogen atom or a linear or branched alkyl group having 1 to 5 carbon atoms, and (e) $R_{11}$ through $R_{16}$ represent independently a hydrogen atom, a halogen atom or an alkoxyl group having 1 to 5 carbon atoms. As specific preferred examples of the spiropiperidine-naphthoxazine compound, there can be mentioned (i) 1,3,3-trimethylspiropiperidine-2,3'-[3H]-naphth-[2,1-b]-1,4-oxazine, (ii) 1-ethyl-3,3-dimethyl-spiropiperidine-2,3'-[3H]-naphth[2,1-b]-1,4-oxazine, (iii) 1-n-propyl-3,3-dimethylspiropiperidine-2,3'-[3H]-naphth[2,1-b]-1,4-oxazine, (iv) 1-isopropyl-3,3-dimethylspiropiperidine-2,3'-[3H]-naphth[2,1-b]-1,4-oxazine, (v) 8'-bromo-1,3,3-trimethylspiropiperidine-2,3'-[3H]-naphth[2,1-b]-1,4-oxazine, (vi) 5'-methoxy-1,3,3-trimethylspiropiperidine-2,3'-[3H]-naphth[2,1-b]-1,4-oxazine, (vii) 9'-methoxy-1,3,3-trimethylspiropiperidine-2,3'-[3H]-naphth[2,1-b]-1,4-oxazine, (viii) 1,2',3,3-tetramethylspiropiperidine-2,3'-[3H]-naphth[2,1-b]-1,4-oxazine, (ix) 5'-methoxy-1,2',3,3-tetramethylspiropiperidine-2,3'-[3H]-naphth-[2,1-b]-1,4-oxazine, (x) 2'-ethyl-1,3,3-trimethylspiropiperidine-2,3'-[3H]-naphth[2,1-b]-1,4-oxazine, and (xi) 2'-ethyl-5'-methoxy-1,3,3-trimethylspiropiperidine-2,3'-[3H]-naphth[2,1-b]-1,4-oxazine.

The spiropiperidine-naphthoxazine compound of the present invention can be prepared in the following manner. More specifically, a spiropiperidine-naphthoxazine compound represented by the general formula (I) can be obtained by condensing a 1-nitroso-2-naphthol represented by the following general formula (IIa):

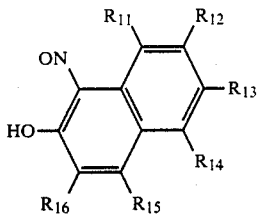

wherein $R_{11}$ through $R_{16}$ are as defined above in the formula (I), or an isomer thereof, that is, a keto-oxime compound, represented by the following general formula (IIb):

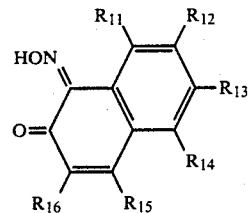

wherein $R_{11}$ through $R_{16}$ are as defined above in the formula (I), with an equimolar amount of a tetrahydropyridinium salt represented by the following general formula (III):

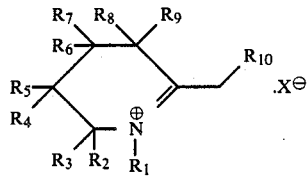

wherein $R_1$ through $R_9$ are as defined above in the formula (I), and X represents an anion such as an iodine anion, a tosylate anion or a methyl sulfate anion, in the presence of a base in a solvent. This condensation reaction is accomplished by heating under reflux in the solvent, through which nitrogen gas is passed in the presence of at least an equimolar amount of the base. If the reaction mixture is cooled after the condensation reaction, a brown crystal is precipitated. The crystal is recovered by filtration and recrystallized from an alcohol (such as methyl alcohol) to obtain a spiropiperidine-naphthoxazine compound represented by the general formula (I).

As the reaction solvent, there can be mentioned polar solvents such as alcohols (for example, methyl alcohol, ethyl alcohol, isopropyl alcohol, n-propyl alcohol, and benzyl alcohol), methyl ethyl ketone, acetone, dimethyl-formamide, dimethylacetamide, and acetonitrile, and nonpolar solvents such as benzene and toluene. As the base, there can be mentioned inorganic bases such as potassium hydroxide and sodium hydroxide, and organic bases such as triethylamine, pyridine, piperidine, and diethylamine.

The spiropiperidine-naphthoxazine compound of the present invention can be dissolved in ordinary organic solvents such as benzene, toluene, chloroform, ethyl acetate, methyl ethyl ketone, acetone, ethyl alcohol, methyl alcohol, isopropyl alcohol, n-butyl alcohol, benzyl alcohol, tetrahydrofuran, dimethylformamide, dimethylsulfoxide, dioxane, acetonitrile, methylcellosolve, morpholine, and ethylene glycol, and each of the obtained solutions is colorless in a dark place but shows a red violet color or blue violet color under irradiation with ultraviolet rays. That is, each solution shows the photochromism phenomenon. The photochromic compound of the present invention can be dissolved in a colorless or transparent solution prepared from a transparent homopolymer or copolymer or a blend thereof and an appropriate solvent, for example, a solution of a polymer as a host material described below, in at least one member selected from the above-mentioned organic solvents. As examples of the solution, there can be mentioned a polyvinyl acetate/acetone solution, a nitrocellulose/acetonitrile solution, a polyvinyl chloride/methyl ethyl ketone solution, a poly(methyl methacrylate)/acetone solution, an acetylcellulose/dimethylformamide solution, a poly(vinyl pyrrolidone)/acetonitrile solution, a polystyrene/benzene solution, and an ethylcellulose/methylene chloride solution.

When the above-mentioned photochromic solution or composition is coated on a transparent support such as triacetylcellulose, polyethylene terephthalate or baryta paper, and is then dried, a photochromic material can be obtained which is colored red violet or blue violet under irradiation with ultraviolet rays and is rendered colorless again if ultraviolet rays irradiation is stopped.

This photochromic material can be easily prepared according to a known optional method. More specifically, the compound represented by the formula (I) is dissolved in, kneaded with, or coated on a host material such as a resin, an oil or fat, or a paper, whereby the compound represented by the general formula (I) can be incorporated into a solid such as a film, a lens or a plate, an oil or fat, a liquid such as an emulsion or other material having an optional shape. The amount of the photochromic compound of the present invention incorporated in a material as described above is not particularly critical, but the photochromic compound is generally incorporated in an amount of $10^{-5}$ to 20% by weight, and preferably, the photochromic compound is incorporated in an amount of $10^{-4}$ to 10% by weight.

The present invention will now be described in detail with reference to the following examples that by no means limit the scope of the invention.

EXAMPLE 1

5.2 g of 1-nitroso-2-naphthol was added to 50 ml of absolute ethyl alcohol through which nitrogen was passed, and the mixture was heated under reflux to completely dissolve 1-nitroso-2-naphthol. A solution comprising 4.2 ml of triethylamine, 8 g of 1,2,3,3-tetramethyl-3,4,5,6-tetrahydropyridinium iodide and 25 ml of absolute ethyl alcohol was gradually added to the above solution over a period of 30 minutes and the mixture was refluxed for 2 hours.

The obtained reaction mixture was cooled and the precipitated brown crystal was recovered by filtration and recrystallized from methanol three times to obtain 3.2 g of a light yellow needle crystal of intended 1,3,3-trimethyl-spiropiperidine-2,3'-[3H]-naphth[2,1-b]-1,4-oxazine.

The physical properties of the obtained compound were as follows.

Melting point: 104° to 105° C.

| Elementary analysis values (%): | | | |
|---|---|---|---|
| | C | H | N |
| theoretical values | 77.52 | 7.53 | 9.51 |
| found values | 77.46 | 7.81 | 9.37 |

H[1]-NMR

The measurement was carried out by using TMS as the internal standard in deuterated dimethylsulfoxide as the solvent by means of a spectrometer, Model R-24B supplied by Hitachi Ltd. The obtained H[1]-NMR spectrum was as shown in FIG. 1.

IR-Spectrum

Figure 2:
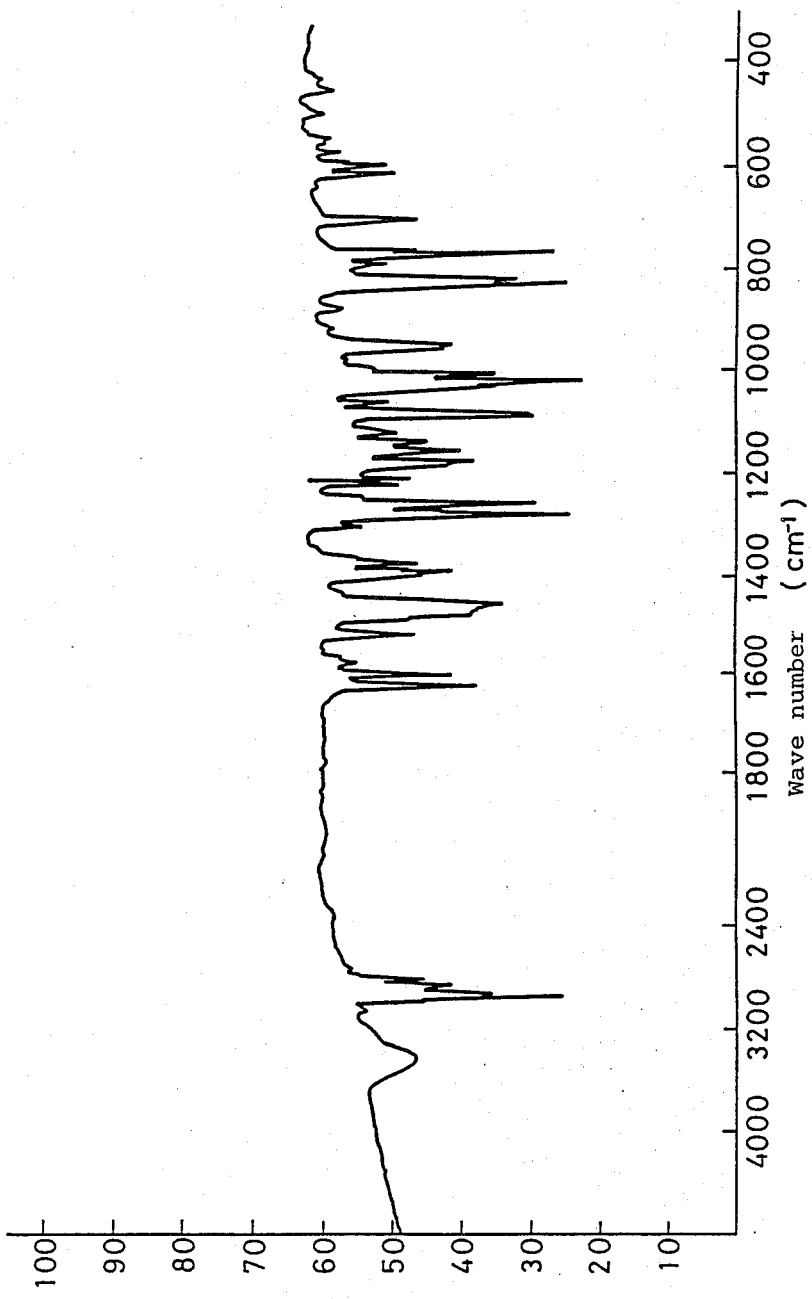
FIG. 2 shows an IR spectrum of this compound.

The measurement was carried out by using an infrared spectrophotometer, Model JASCO A-3. The IR spectrum was as shown in FIG. 2.

Visible ray absorption spectrum

Figure 3:
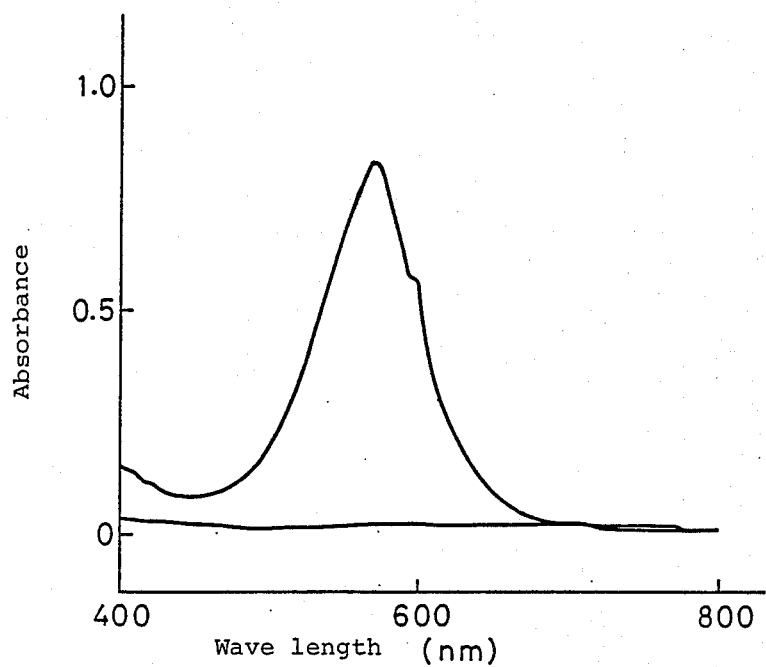
FIG. 3 shows a visible ray absorption spectrum of this compound.

The visible ray absorption spectrum in a methyl alcohol solution before and after irradiation with ultraviolet rays was measured by using an ultraviolet/visible spectrophotometer, Model 320 supplied by Hitachi Ltd. The concentration was $5 \times 10^{-5}$ mole/l and the measurement temperature was 25° C. The obtained visible ray absorption spectrum was as shown in FIG. 3.

Decolorization speed

The decolorization speed and half-value period were determined from the change with the lapse of time of the absorbency at the visible absorption maximum wavelength after irradiation with ultraviolet rays. The results obtained in various solvents are shown in Table 1. The concentration was $5 \times 10^{-5}$ mole/l and the temperature was 25° C.

TABLE 1

| Solvent | λmax (nm) | K (S$^{-1}$) | t½ [S] |
|---|---|---|---|
| Methanol | 560 | $6.15 \times 10^{-2}$ | 11 |
| Isopropyl alcohol | 560 | $5.78 \times 10^{-1}$ | 1.2 |
| Benzyl alcohol | 575 | $3.50 \times 10^{-2}$ | 20 |
| Dimethylsulfoxide | 575 | $1.86 \times 10^{-1}$ | 3.7 |
| Toluene | 580 | 1.16 | 0.6 |

Adaptability to repeated use

Figure 4:
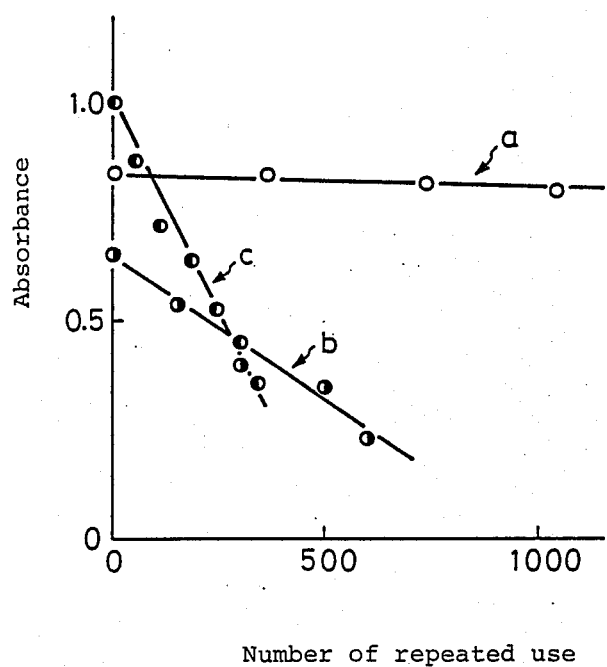
FIG. 4 is a diagram illustrating the adaptability of the compound (a) prepared in Example 1 to repeated use, in contrast to that of the compounds (b) and (c) obtained in Comparative Examples 1 and 2.

An XeCl exicimer laser, supplied by Lambda Physique, was used as the ultraviolet ray irradiation source. The absorbency at a wavelength of 560 nm just after irradiation was recorded by a storage oscilloscope supplied by Sony Tectronics. The solvent was isopropyl alcohol, the concentration was $5 \times 10^{-5}$ mole/l, and the measurement temperature was 25° C. The results of the measurement of the relationship between the absorbency just after irradiation with ultraviolet rays and the frequency of repetition were as shown in FIG. 4-(a).

For comparison, the results of the measurement made on the compound (Comparative Example 1) of the following formula:

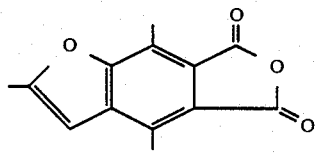

and the compound (Comparative Example 2) of the following formula:

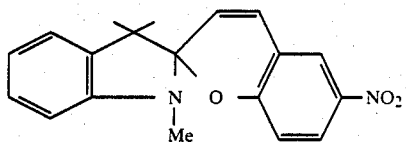

were shown in FIGS. 4-(b) and 4-(c), respectively.

EXAMPLE 2

3.46 g of 1-nitroso-2-naphthol was added to 35 ml of absolute ethyl alcohol through which nitrogen was passed, and the mixture was heated and refluxed to completely dissolve the 1-nitroso-2-naphthol. A solution comprising 2.8 ml of triethylamine, 5.62 g of 1-ethyl-2,3,3-trimethyl-3,4,5,6-tetrahydropyridinium iodide, and 20 ml of absolute ethyl alcohol was gradually added to the above solution over a period of 25 minutes, and the mixture was refluxed for 2 hours.

The obtained reaction mixture was cooled, and the precipitated brown crystal was recovered by filtration and recrystallized from methanol three times to obtain 2.5 g of a light yellow needle crystal of intended 1-ethyl-3,3-dimethylspiropiperidine-2,3'-[3H]-naphth[2,1-b]-1,4-oxazine.

The physical properties of the obtained compound were as follows.

Melting point: 102° to 103° C.

| Elementary analysis values (%): | | | |
|---|---|---|---|
| | C | H | N |
| calculated value | 77.89 | 7.84 | 9.08 |
| found values | 77.58 | 7.92 | 8.96 |

H[1]-NMR

The measurement was carried out in the same manner as described in Example 1.

δ(ppm): 0.8 (s, 3H), 1.2 (s, 3H), 0.9–1.3 (t, 3H), 2.2–2.6 (q, 2H), 1.3–3.0 (b, 6H), 6.3–8.5 (m, 7H)

EXAMPLE 3

3.46 g of 1-nitroso-2-naphthol was added to 35 ml of absolute ethyl alcohol through which nitrogen was passed and the mixture was heated and refluxed to completely dissolve the 1-nitroso-2-naphthol. A solution comprising 2.8 ml of triethylamine, 6.45 g of 1-n-propyl-2,3,3-trimethyl-3,4,5,6-tetrahydropyridinium iodide, and 20 ml of absolute ethyl alcohol was gradually added to the above-solution over a period of 25 minutes and the mixture was refluxed for 2 hours.

The obtained reaction mixture was cooled, and the precipitated brown crystal was recovered by filtration and recrystallized from methanol three times to obtain 2.2 g of a light yellow needle crystal of intended 1-n-propyl-3,3-dimethylspiropiperidine-2,3'-[3H]-naphth[2,1-b]-1,4-oxazine.

The physical properties of the obtained compound were as follows.

Melting point: 101° to 102° C.

| Elementary analysis values (%) | | | |
|---|---|---|---|
| | C | H | N |
| calculated values | 78.22 | 8.13 | 8.69 |

| Elementary analysis values (%) | | | |
|---|---|---|---|
| | C | H | N |
| found values | 78.52 | 7.89 | 8.44 |

H¹-NMR

δ(ppm): 0.8 (s, 3H), 1.2 (s, 3H), 0.7–1.1 (t, 3H), 1.1–1.7 (m, 2H), 2.5–2.8 (t, 2H), 1.0–3.0 (b, 6H), 6.3–8.5 (m, 7H)

EXAMPLE 4

3.46 g of 1-nitroso-2-naphthol was added to 35 ml of absolute ethyl alcohol through which nitrogen was passed, and the mixture was heated and refluxed to completely dissolve the 1-nitro-2-naphthol. A solution comprising 2.8 ml of triethylamine, 5.90 g of 1-isopropyl-2,3,3-trimethyl-3,4,5,6-tetrahydropyridinium iodide, and 20 ml of absolute ethyl alcohol was gradually added to the above solution over a period of 25 minutes, and the mixture was refluxed for 2 hours.

The obtained reaction mixture was cooled, and the precipitated brown crystal was recovered by filtration and recrystallized from methanol three times to obtain 1.3 g of a light yellow needle crystal of intended 1-isopropyl-3,3-dimethylspiropiperidine-2,3'-[3H]-naphth[2,1-b]-1,4-oxazine.

The physical properties of the obtained compound were as follows.

Melting point: 100° to 101° C.

| Elementary analysis values (%): | | | |
|---|---|---|---|
| | C | H | N |
| calculated values | 78.22 | 8.13 | 8.69 |
| found values | 77.97 | 8.11 | 8.89 |

H¹-NMR

δ(ppm): 0.8 (s, 3H), 1.2 (s, 3H), 0.9–1.3 (d, 6H), 2.7–3.3 (m, 1S), 1.0–3.0 (b, 6H), 6.3–8.5 (m, 7H)

EXAMPLE 5

5.04 g of 6-bromo-1-nitroso-2-naphthol was added to 35 ml of absolute ethyl alcohol through which nitrogen was passed, and the mixture was heated and refluxed to completely dissolve the 6-bromo-1-nitroso-2-naphthol. A solution comprising 2.8 ml of triethylamine, 5.34 g of 1,2,3,3-tetramethyl-3,4,5,6-tetrahydropyridinium iodide and 20 ml of absolute ethyl alcohol was gradually added to the above solution over a period of 30 minutes, and the mixture was refluxed for 2 hours.

The obtained reaction mixture was cooled, and the precipitated brown crystal was recovered by filtration and recrystallized from methanol three times to obtain 2.6 g of a light yellow needle crystal of intended 8'-bromo-1,3,3-trimethylspiropiperidine-2,3'-[3H]-naphth[2,1-b]-1,4-oxazine.

The physical properties of the obtained compound were as follows.

Melting point: 108° to 109° C.

| Elementary analysis values (%) | | | |
|---|---|---|---|
| | C | H | N |
| calculated values | 61.13 | 5.67 | 7.50 |
| found values | 61.33 | 5.70 | 7.32 |

H¹-NMR

δ(ppm): 0.8 (s, 3H), 1.2 (s, 3H), 2.1 (s, 3H), 1.0–3.0 (b, 6H), 6.3–8.5 (m, 6H)

EXAMPLE 6

4.06 g of 3-methoxy-1-nitroso-2-naphthol was added to 35 ml of absolute ethyl alcohol through which nitrogen was passed and the mixture was heated and refluxed to completely dissolve the 3-methoxy-1-nitroso-2-naphthol. A solution comprising 2.8 ml of triethylamine, 5.34 g of 1,2,3,3-tetramethyl-3,4,5,6-tetrahydropyridinium iodide, and 20 ml of absolute ethyl alcohol was gradually added to the above solution over a period of 25 minutes and the mixture was refluxed for 2 hours.

The obtained reaction mixture was cooled, and the precipitated brown crystal was recovered by filtration and recrystallized from methanol three times to obtain 2.6 g of a light yellow needle crystal of intended 5'-methoxy-1,3,3-trimethylspiropiperidine-2,3'-[3H]-naphth[2,1-b]-1,4-oxazine.

The physical properties of the obtained compound were as follows.

Melting point: 98° to 99° C.

| Elementary analysis values (%) | | | |
|---|---|---|---|
| | C | H | N |
| calculated values | 74.05 | 7.46 | 8.63 |
| found values | 73.54 | 7.12 | 8.41 |

H¹-NMR

δ(ppm): 0.8 (s, 3H), 1.2 (s, 3H), 2.1 (s, 3H), 1.0–3.0 (b, 6H), 3.8 (s, 3H), 6.3–8.5 (m, 6H)

EXAMPLE 7

4.06 g of 7-methoxy-1-nitroso-2-naphthol was added to 35 ml of absolute ethyl alcohol through which nitrogen was passed, and the mixture was heated and refluxed to completely dissolve the 7-methoxy-1-nitroso-2-naphthol. A solution comprising 2.8 ml of triethlamine, 5.34 g of 1,2,3,3-tetramethyl-3,4,5,6-tetrahydropyridinium iodide, and 20 ml of absolute ethyl alcohol was gradually added to the above solution over a period of 25 minutes, and the mixture was refluxed for 2 hours.

The obtained reaction mixture was cooled, and the precipitated brown crystal was recovered by filtration and recrystallized from methanol three times to obtain 1.9 g of a light yellow needle crystal of intended 9'-methoxy-1,3,3-trimethylspiropiperidine-2,3'-[3H]-naphth[2,1-b]-1,4-oxazine.

The physical properties of the obtained compound were as follows.

Melting point: 105° to 106° C.

| Elementary analysis values (%): | | | |
|---|---|---|---|
| | C | H | N |
| calculated values | 74.05 | 7.46 | 8.63 |
| found values | 73.72 | 7.33 | 8.51 |

H¹-NMR

δ(ppm): 0.8 (s, 3H), 1.2 (s, 3H), 2.1 (s, 3H), 1.0–3.0 (b, 6H), 4.0 (s, 3H), 6.3–8.5 (m, 6H)

EXAMPLE 8

3.46 g of 1-nitroso-2-naphthol was added to 35 ml of absolute ethyl alcohol through which nitrogen was passed, and the mixture was heated and refluxed to completely dissolve the 1-nitroso-2-naphthol. A solution comprising 2.8 ml of triethylamine, 5.62 g of 2-ethyl-1,3,3-trimethyl-3,4,5,6-tetrahydropyridinium iodide, and 20 ml of absolute ethyl alcohol was gradually added to the above solution over a period of 25 minutes and the mixture was refluxed for 2 hours.

The obtained reaction mixture was cooled, and the precipitated brown crystal was recovered by filtration and recrystallized from methanol three times to obtain 0.5 g of a light yellow needle crystal of intended 1,2',3,3-tetramethylspiropiperidine-2,3'-[3H]-naphth[2,1-b]-1,4-oxazine.

The physical properties of the obtained compound were as follows.

Melting point: 103° C.

| Elementary analysis values (%): | | | |
| --- | --- | --- | --- |
| | C | H | N |
| calculated values | 77.89 | 7.84 | 9.08 |
| found values | 77.56 | 7.79 | 8.82 |

H$^1$-NMR

δ(ppm): 0.8 (s, 3H), 1.2 (s, 3H), 2.1 (s, 3H), 2.4 (s, 3H), 1.0–3.0 (b, 6H), 6.3–8.5 (m, 7H)

EXAMPLE 9

4.06 g of 3-methoxy-1-nitroso-2-naphthol was added to 35 ml of absolute ethyl alcohol through which nitrogen was passed, and the mixture was heated to completely dissolve the 3-methoxy-1-nitroso-2-naphthol. A solution comprising 2.8 ml of triethylamine, 5.62 g of 2-ethyl-1,3,3-trimethyl-3,4,5,6-tetrahydropyridinium iodide, and 20 ml of absolute ethyl alcohol was gradually added to the above solution over a period of 25 minutes, and the mixture was refluxed for 2 hours.

The obtained reaction mixture was cooled, and the precipitated brown crystal was recovered by filtration and recrystallized from methanol three times to obtain 0.7 g of a light yellow needle crystal of intended 5'-methoxy-1,2',3,3-tetramethylspiropiperidine-2,3'-[3H]-naphth[2,1-b]-1,4-oxazine.

The physical properties of the obtained compound were as follows.

Melting point: 94° to 95° C.

| Elementary analysis values (%): | | | |
| --- | --- | --- | --- |
| | C | H | N |
| calculated values | 74.53 | 7.74 | 8.28 |
| found values | 74.21 | 7.53 | 8.02 |

H$^1$-NMR

δ(ppm): 0.8 (s, 3H), 1.2 (s, 3H), 2.1 (s, 3H), 2.4 (s, 3H), 1.0–3.0 (b, 6H), 3.8 (s, 3H), 6.3–8.5 (m, 6H)

EXAMPLE 10

3.46 g of 1-nitroso-2-naphthol was added to 35 ml of absolute ethyl alcohol through which nitrogen was passed, and the mixture was heated and refluxed to completely dissolve the 1-nitroso-2-naphtol. A solution comprising 2.8 ml of triethylamine, 5.90 g of 2-n-propyl-1,3,3-trimethyl-3,4,5,6-tetrahydropyridinium iodide, and 20 ml of absolute ethyl alcohol was gradually added to the above solution over a period of 25 minutes, and the mixture was refluxed for 2 hours.

The obtained reaction mixture was cooled, and the precipitated brown crystal was recovered by filtration and recrystallized from methanol three times to obtain 0.4 g of a light yellow needle crystal of intended 2'-ethyl-1,3,3-trimethylspiropiperidine-2,3'-[3H]-naphth[2,1-b]-1,4-oxazine.

The physical properties of the obtained compound were as follows.

Melting point: 98° to 99° C.

| Elementary analysis values (%) | | | |
| --- | --- | --- | --- |
| | C | H | N |
| calculated values | 78.22 | 8.13 | 8.69 |
| found values | 77.98 | 7.86 | 8.39 |

H$^1$-NMR

δ(ppm): 0.8 (s, 3H), 1.2 (s, 3H), 1.1–1.5 (m, 3H), 2.1 (s, 3H), 2.8–3.1 (q, 2H), 1.0–3.0 (b, 6H) 6.3–8.5 (m, 7H)

EXAMPLE 11

4.06 g of 3-methoxy-1-nitroso-2-naphthol was added to 35 ml of absolute ethyl alcohol through which nitrogen was passed, and the mixture was heated and refluxed to completely dissolve the 3-methoxy-1-nitroso-2-naphthol. A solution comprising 2.8 ml of triethylamine, 5.90 g of 2-n-propyl-1,3,3-trimethyl-3,4,5,6-tetrahydropyridinium iodide, and 20 ml of absolute ethyl alcohol was gradually added to the above solution over a period of 25 minutes, and the mixture was refluxed for 2 hours.

The obtained reaction mixture was cooled, and the precipitated brown crystal was recovered by filtration and recrystallized from methanol three times to obtain 0.5 g of a light yellow needle crystal of intended 2'-ethyl-5'-methoxy-1,3,3-trimethylspiropiperidine-2,3'-[3H]-naphth[2,1-b]-1,4-oxazine.

The physical properties of the obtained compound were as follows.

Melting point: 92° to 93° C.

| Elementary analysis values (%): | | | |
| --- | --- | --- | --- |
| | C | H | N |
| calculated values | 74.97 | 8.01 | 7.95 |
| found values | 74.65 | 7.95 | 7.54 |

H$^1$-NMR

δ(ppm): 0.8 (s, 3H), 1.2 (s, 3H), 1.1–1.5 (m, 3H), 2.1 (s, 3H), 2.8–3.1 (q, 2H), 3.8 (s, 3H), 6.3–8.5 (m, 6H)

CAPABILITY OF EXPLOITATION IN INDUSTRY

The spiropiperidine-naphthoxazine compound of the present invention is a photochromic compound having an excellent adaptability to repeated use, and this compound can be preferably used for automatic light quantity-adjusting plastic sun glasses, skiing goggles, sun visors, window panes, laminated glass sheets, packaging materials for foods, drinks and medicines, decorative articles, automobile trims, paints, inks, cosmetics such as manicures and lip sticks, and writable and erasable memory materials.

We claim:

1. A spiropiperidine-napthoxazine compound represented by the following general formula (I):

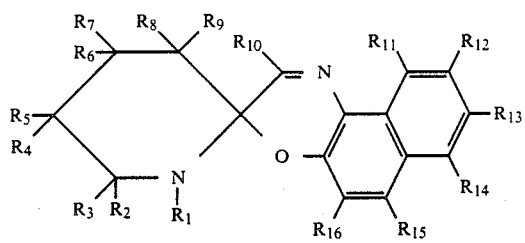

(I)

wherein (a) $R_1$ represents a linear or branched alkyl group having 1 to 18 carbon atoms, an aralkyl group having 7 to 15 carbon atoms, which may be substituted, an alkenyl group having 1 to 10 carbon atoms or an aryl group having 6 to 15 carbon atoms, which may be substituted, (b) $R_2$, $R_3$, $R_4$, $R_5$, $R_6$, $R_7$, $R_8$, and $R_9$ represent independently a group $R_1$ defined above, a hydrogen atom or an alicyclic ring having 5 to 10 carbon atoms or a norbonyl or adamantyl group, which norbonyl or adamantyl group is bonded between groups present on one skeleton carbon atom or between groups on adjacent skeleton carbon atoms (at the ortho-position), (c) $R_{10}$ represents a hydrogen atom, a linear or branched alkyl group having 1 to 18 carbon atoms, an aralkyl group having 7 to 15 carbon atoms, which may be substituted, or an alkenyl group having 1 to 10 carbon atoms, and (d) $R_{11}$, $R_{12}$, $R_{13}$, $R_{14}$, $R_{15}$, and $R_{16}$ represent independently a hydrogen atom, a linear or branched alkyl group having 1 to 9 carbon atoms, an alkoxyl group having 1 to 5 carbon atoms, a halogen atom, a nitro group or a cyano group, said substituents present on the above recited groups which may be substituted being those substituents which do not adversely affect photochromic properties.

2. A compound as set forth in claim 1, wherein in the general formula (I), (a) $R_1$ represents a linear or branched alkyl group having 1 to 4 carbon atoms, (b) $R_2$, $R_3$, $R_4$, $R_5$, $R_6$, and $R_7$ represent independently a hydrogen atom, a methyl group or an ethyl group, (c) $R_8$ and $R_9$ represent independently a methyl group or an ethyl group, (d) $R_{10}$ represent a hydrogen atom or a linear or branched alkyl group having 1 to 5 carbon atoms, and (e) $R_{11}$ through $R_{16}$ represent independently a hydrogen atom, a halogen atom or an alkoxyl group having 1 to 5 carbon atoms.

* * * * *